United States Patent [19]

Donahoe et al.

[11] Patent Number: 4,510,131

[45] Date of Patent: Apr. 9, 1985

[54] PURIFIED MULLERIAN INHIBITING SUBSTANCE AND METHOD OF USE

[75] Inventors: Patricia K. Donahoe, Weston; Gerald P. Budzik, Waltham; David A. Swann, Lexington, all of Mass.

[73] Assignee: The General Hospital Corporation, Boston, Mass.

[21] Appl. No.: 512,553

[22] Filed: Jul. 11, 1983

Related U.S. Application Data

[62] Division of Ser. No. 287,943, Jul. 29, 1981, Pat. No. 4,404,188.

[51] Int. Cl.$^3$ .................. A61K 37/02; C07G 7/00; C12Q 1/29
[52] U.S. Cl. ......................... 424/105; 260/112 R; 435/29; 514/8
[58] Field of Search .................. 424/105, 177; 260/112 R; 435/29

[56] References Cited

PUBLICATIONS

Donahoe et al.,–Chem. Abst. vol. 96 (1982) p. 63164j.
Swann et al.,–Chem. Abst. vol. 90 (1979) p. 199833k.
Swann et al., *Developmental Biology*, 69: 73–84 (1979).
Donahoe, et al., *Annals of Surgery*, 194: 472–480 (Oct. 1981).
Fuller, Jr., et al., *Gynecologic Oncology*, 17: 124–132 (1984).
Budzik, et al., *Cell* 21: 909–915 (Oct. 1980).
Donahoe, et al., *Science*, 205: 913–915.
Donahoe, et al., *Biology of Reproduction*, 16: 238–243 (1977).
Picard, et al., *Biomedicine*, 25: 147–150 (1976).
Josso, *Journal of Clinical Endocrinology*, 31: 265–270 (1972).
Josso, et al., "In Vitro Synthesis of Mullerian-Inhibiting Hormone by Seminiferous Tubes Isolated from the Calf Fetal Testis," *Endocrinology*, 94: 829–834 (1973).
Mudgett-Hunter et al., 1981 FASCP Abstract, "Monoclonal Antibody to Mullerian Inhibiting Substance" (Apr. 1981).
Donahoe, et al., *Pediatric Andrology*, Martinus Nyoff Publishers, The Hague/Boston/London, pp. 37–46 (1981).
Rosenwaks, *Journal of Clinical Endocrinology and Metabolism*, 52: 817 (1981).
Rosenwaks et al., Abstract 174, 65th Annual Meeting *Program and Abstracts*, Jun. 8, 1983.
Fuller et al., *Gynecologic Oncology*, Mullerian Inhibiting Substance Inhibition of a Human Endometrial Carcinoma Cell Line Xenografted in Nude Mice," 1984. (preprint).

*Primary Examiner*—Sam Rosen
*Attorney, Agent, or Firm*—Saidman, Sterne, Kessler & Goldstein

[57] ABSTRACT

A process for purifying Mullerian Inhibiting Substance (MIS) from testicular tissue which comprises incubating testicular tissue in a culture media in the presence of a protease inhibitor in order to extract MIS from the tissue, chromatographing the extract on an anionic exchange resin followed by chromatographing the biologically active product obtained therefrom on a cationic exchange resin; the biologically active material from the cationic exchange resin is chromatographed by lectin affinity chromatography on wheat germ lectin and then either chromatographed by lectin affinity chromatography on concanavalin A or by triazinyl dye affinity chromatography on a appropriate triazinyl dye; MIS is obtained in 8,000-fold and 15,000-fold purification over original testicular tissue.

3 Claims, 13 Drawing Figures

PURIFIED MULLERIAN INHIBITING SUBSTANCE AND METHOD OF USE

This is a division of application Ser. No. 287,943 filed July 29, 1981, now U.S. Pat. No. 4,404,188.

BACKGROUND OF THE INVENTION

1. Field of the Invention

The present invention relates to purified Mullerian Inhibiting Substance, methods for its purification and its use in the inhibition of tumor growth.

2. Description of the Prior Art

A substance with the properties of inducing regression of the Mullerian duct, the fetal analog of the uterus, fallopian tube and vagina, was suspected in 1916 when Lillie (Science 43:611–613 (1916)) described the freemartin calf, an abnormal female product of heterosexual twinning, long known to farmers and veterinarians. Immunologists soon appreciated the chimeric characteristics of this "experiment in nature", and endocrinologists began to understand the important developmental implications of this masculinized female.

Jost, A. (CR Soc. Biol. 140:460, 463 (1946), ibid 141:135 (1947)), experimentally reproduced selected freemartin effects in embryo rabbits at a stage when they were sexually indifferent, by removing gonads and replacing them with either testis, ovary, no gonad, or crystalline testosterone. Those replaced with ovary or no gonad developed normal Mullerian ducts which later formed uterus, fallopian tubes and vagina. Those replaced with testis developed Wolffian ducts which later formed vas, seminal vesicals, and epididymis, while the Mullerian ducts regressed. Those replaced with testosterone alone stimulated the Wolffian duct structures but did not regress the Mullerian duct. These results caused Jost to speculate the existence of a testicular product which caused regression of the Mullerian duct, coining the term "Mullerian Inhibiting Substance" (MIS).

Donahoe et al (J. Surg. Res. 23:141–148 (1977)) demonstrated that a high level of MIS persists in newborn calf testis for up to 8 weeks after birth. This tissue has provided a ready source for the partial purification and characterization of the biologically active moiety by guanidine hydrochloride extraction (see for example Swann, D. A. et al, Developmental Biology 69:73–84 (1979), Donahoe et al, Pediatric Andrology 37–46, 1981 Martinus Nijhoff Publishers, The Hague/Boston/London, and Donahoe et al, Science:205, 913–915 (1979)).

Purification of MIS from calf testis has been a tedious undertaking since large quantities of material are consumed in the vital assay required for activity confirmation. In spite of these problems, interest in MIS purification remains high since impure fractions with MIS activity are cytotoxic to human ovarian cancer in vitro (Donahoe, P. K., et al Science 205:913–915 (1979)).

Incubation of fetal calf testis in media for 4 hours showed that MIS can also be secreted (Josso, N. et al, Biol. Reprod. 13:163–167 (1975)). Homogenization of testis tissue, however, has not yielded active preparations (Donahoe, P. K. et al Cryobiol. 14:534–542 (1977), Josso, N. et al, Recent Prog. Hormone Res. 33:117–167 (1977)).

The aforementioned previous attempts at the purification of MIS yielded preparations with only approximate 30-fold enhancement in purity. Furthermore, the use of guanidine hydrochloride as a disassociative solvent in the extraction of testicular tissue, is a method which although instructive, requires a subsequent lengthy cesium chloride sedimentation prior to further fractionation.

Because of the great applicability of purified MIS, and the need to streamline the process of purification, there continues to exist a need for an efficient method of purification for, and highly purified fractions of this material.

SUMMARY OF THE INVENTION

It is therefore an object of the present invention to provide improved methods of purification of Mullerian Inhibiting Substance (MIS) from testicular tissue.

It is another object of the invention to provide highly purified compositions comprising MIS bioactive fractions.

Yet another object of the invention is to provide improved methods of treating certain carcinomas especially ovarian carcinomas.

These and other objects of the invention as will hereinafter become more readily apparent have been attained by providing:

A process for purifying biologically active Mullerian Inhibiting Substance (MIS) from testicular tissue which comprises:

(a) Incubating testicular tissue in an appropriate aqueous culture media in the presence of a protease inhibitor, for a time sufficient to extract MIS from said tissue into said media;

(b) Chromatographing an aqueous solution of the extracted MIS on an anion exchange resin and collecting unbound fractions containing said biologically active MIS;

(c) Chromatographing said unbound biologically active fraction from said anion exchange resin on a cation exchange resin, and collecting unbound fractions containing said biologically active MIS.

The invention has also been attained by providing a process as described hereinbefore which, after said step (c) comprises:

(d) Chromatographing said fraction obtained from said step (c) on a solid phase supported wheat germ lectin and eluting MIS fraction bound to said lectin with a ligand capable of binding to said lectin and displacing said MIS therefrom.

The invention has also been attained by providing a process as provided in the previous paragraph which, after said step (d) further comprises:

(e) Chromatographing said MIS fraction obtained from step (d) on solid phase-supported Concanavalin A, and eluting the MIS fraction bound to said Concanavalin A with a ligand capable of binding to said Concanavalin A and of displacing said MIS therefrom.

Still another object of the invention has been obtained by providing a process as described in the next to the last paragraph hereinbefore which, after said step (d) further comprises:

(f) Chromatographing said MIS fraction obtained from said step (d), on a solid-phase supported triazinyl dye capable of binding said MIS material, in the presence of a thiol-reducing compound and at an inorganic salt concentration which is sufficiently low to allow binding of said MIS material to said solid phase bound dye; and eluting MIS fraction bound to said solid phase bound dye by increasing the inorganic salt concentration to a level sufficient to desorb said MIS material from said dye.

Other objects of the invention have also been attained by providing:

A composition comprising Mullerian Inhibiting Substance (MIS) derived from testicular tissue having an activity of at least 1 as measured by the Mullerian organ regression test, being substantially free of albumin and being about 7,000–8,000-fold enriched in MIS activity over natural testicular tissue per dry weight of said tissue.

Yet other objects of the invention have been attained by providing:

A composition comprising Mullerian Inhibiting Substance derived from testicular tissue having an activity of at least 2–2.5 as measured by the Mullerian regression organ test;

being substantially free of albumin and of proteinaceous material having a molecular weight of 35,000±10,000 Daltons, and 70,000±10,000 Daltons; and being about 15,000-fold enriched in MIS activity over natural testicular tissue per dry weight of said tissue.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 4 shows the polyacrylamide SDS gel electrophoresis of active column fractions through the Concanavalin A steps of FIG. 3. Gel A is the incubation media, gel B is the DEAE-I fraction, gel C is the CM-I fraction, gel D is the wheat germ lectin fraction II, gel E is the concanavalin A fraction II. Approximately 50 micrograms of sample were denatured with SDS and reduced with 2-mercaptoethanol (5 min, 100° C.) prior to loading on a 10% polyacrylamide slab gel topped with 3% stacking gel. The gel was run at constant current of 30 mAmps/gel and was subsequently fixed for 3 hours in 50% trichloracetic acid (TCA) and protein-stained with Coomassie Blue (0.25% in 50% TCA). Molecular weights of simultaneously electrophoresed standards are indicated. (F) gel is the Concanavalin A-II fraction electrophoresed without prior reduction.

DESCRIPTION OF THE PREFERRED EMBODIMENTS

The present invention provides an improved process for the purification of MIS from testicular tissue which avoids the use of extraction processes with strongly disassociating solvents, as described by Donahoe et al in Science 205:913-915 (1979) and by Donahoe et al, U.S. patent application Ser. No. 071,316 filed Aug. 30, 1979 for "Purified Mullerian Inhibiting Substance And Process For Treating Human Ovarian Cancer Cells". The latter application is herein incorporated by reference.

The materials prepared at different stages of the process of the present invention are all distinct embodiments of the present invention, and they can all be used for the treatment of ovarian carcinoma in animals.

The process of the invention comprises excising testicular tissue from the newborn animals (preferably newborn calf testes) and thereafter incubating said testes in culture media for short periods of time (30 min.–2 hr.) at physiological temperatures (25°–37° C., preferably 37° C.). The media should contain amino acids, vitamins and isotonic salts. Examples of incubation media include DMEM, Basal Media Eagle's, CMRL 1066 or MEM. Increasing the incubation time to about 90 min. does not increase assayable MIS activity in the media. The addition of a protease inhibitor (such as benzamidine at 1–10 mM, preferably 5 mM) immediately following the incubation is essential for consistent recovery of MIS preparations with high bioactivity.

The guanidine hydrochloride extractions of the prior art result in nearly complete cellular disruption, and release of large amounts of nucleic acid, and necessitate an obligatory cesium chloride density sedimentation. The process from extraction through fractionation of the cesium chloride gradient requires about 48 hrs. to complete and leads to lower biological activities in the MIS fractions isolated. The media incubation procedure of the present invention on the other hand, can be performed in less than 1 hr. followed by an overnight centrifugation, and consistently yields a concentrated media fraction with high bioactivity, as shown in Table I.

TABLE I
PURIFICATION OF MULLERIAN INHIBITING SUBSTANCE

| Fraction[a] | Total Protein (mg)[b] | Purification Factor | Biological Activity |
|---|---|---|---|
| testis tissue (40) | 14000.0 | | 5+ |
| incubation media | 1245.7 | 11.2 | 3–4+ |
| CM-I | 329.4 | 42.5 | 3–4+ |
| WGL-II | 28.6 | 489.5 | 2–3+ |
| Con A-II | 1.8 | 7777.7 | 2+ |

[a]Fraction designations are those used in the text.
[b]Weight of testis tissue is based on the average dry weight of 350 mg per testis. All other values for total protein were It is substantially impossible to detect any MIS bioctivity in the tissue residue following media incubation and centrifugation. Furthermore, when the tissue pellet is subjected to the same extraction as the sedimentation procedure which is successful when applied to fresh tissue (Donahoe et al, supra) it is no longer possible to recover any additional MIS activity.

the next step in the process is the sequential treatment of the supernatant extract (appropriately separated from the tissue pellet), by anion, and then by cation exchange chromatography. Swann et al (Developmental Biology 69:73-84 (1979)) reported the treatment of partially purified MIS fractions on anion exchange chromatography. The highest purification factor, coupled with the optimal retention of MIS biological activity, however, is obtained when *both* anion as well as cation exchange chromatography are performed in the presence of an appropriate inorganic salt such as sodium chloride, potassium chloride, sodium bromide, and the like. Zn salts should be avoided, as MIS appears to be sensitive to $Zn^{+2}$. Ideally the concentration of salt is 0.01–0.01M, most preferably 0.05M. The preferred salt is sodium chloride. Chromatography is carried out in an appropriate physiologically compatible buffer, such as PBS, or the like, at physiological pH, e.g, 6.0–8.5.

The concentrated incubation media obtained from the first incubation step (the extract), is normally rapidly equilibrated by desalting by any appropriate desalting method. A preferred method is passage of the medium through a gel filtration chromatographic column such as a Sephadex G-25 ® column prior to anion exchange chromatography. This procedure is preferred but alternative to an overnight dialysis. It is faster and preserves MIS bioctivity. The equilibrated, desalted material is loaded on an appropriate anionic exchange chromatographic column such as for example DEAE Bio-Gel A ®. Biological activity is detected only in the unbound fraction and is found invariably at the same levels as in the extract incubation media (Table I, supra). The inactive bound fraction can be eluted with a step increase of ionic strength to 10-fold over the base concentration. A linear sodium chloride gradient offers no advantage in the retrieval of bioactive material.

Following the anion exchange separation, the biologically active fraction obtained therefrom is further fractionated under similar buffer conditions by cation exchange resin, chromatography on an appropriate cationic exchange such as carboxymethyl Bio-Gel A[r]. The MIS bioctivity is again completely recovered in the unbound fraction (hereinafter fraction "CM-1") and at the same 3–4+ bioctivity level as in the two preceeding steps (Table I, supra). Activity is never detected in the other two column fractions, and, again, linear salt gradients offer no advantage over a single step elution.

A larger enhancement in purification is obtained following sequential lectin affinity chromatography. This chromatography confirms that the major component in the biologically active fraction is a glycoprotein which comprises primarily mannose, galactose, glucoseamine and N-acetyl neuraminic acid (Donahoe et al, U.S. patent application Ser. No. 071,316, supra).

Lectin affinity chromatography is well known to those skilled in the art, and comprises contacting the glycoprotein-containing material with a glycoprotein-binding lectin immobilized on a solid support.

It is preferred to carry out a first chromatographic step using wheat germ lectin bound on a solid support such as for example Sepharose[r] 6MB. Under these conditions most of the loaded protein passes directly through the lectin column with PBS elution and contains no MIS activity. Ligand elution is then carried out with any ligand capable of binding to wheat germ lectin and thereby displacing the glycoproteinaceous MIS therefrom. It is preferred to use N-acetyl glucosamine as the elution ligand, (50–500 mg/ml, preferably 100 mg/ml). This yields a glycoprotein fraction (hereinafter "WGL-II") containing a high level of MIS biological activity, see Table I, supra.

After this step, the process can take either of two alternatives. In one alternative, the WGL-II fraction is treated with Concanavalin A, or, in the other alternative, the WGL-II fraction is treated by dye affinity chromatography.

In the first alternative, WGL-II is contacted with insolubilized Concanavalin A (such as Concanavalin A-Sepharose 4B®) and, as with wheat germ lectin affinity chromatography, the MIS biological activity is retrieved only in the bound peak protein fraction (hereinafter "Con A-II") after column elution with a lectin specific sugar (0.1–0.5M, preferably 0.2M) which has the ability to bind to Concanavalin A and thereby displace the glycoproteinaceous MIS therefrom. It is preferred to use a methyl-α-D-glucoside, such as 1-O-methyl-α-D glucopyranoside. Activity is never detected in the unbound protein fraction (hereinafter "Con A-I"). The Con A-II fractions are enriched about 8,000-fold per dry gram weight basis over the original testicular tissue, Table I, supra.

When dye affinity chromatography is used (the second alternative after WGL-II preparation) a fraction enriched 15,000-fold can be obtained. Fraction WGL-II is concentrated and dialyzed against PBS containing 1-25 mM, preferably 5-10 mM, of 2-mercaptoethanol. This material is loaded on a column having an immobilized triazinyl dye as the ligand. Immobilized triazinly dyes are commercially available in the art (Amicon, sold as Matrex Gel®). These dyes are known to bind serum proteins. The present inventors, however, discovered that quite unexpectedly, the MIS bioactivity also binds thereon and can therefore be separated from other, non-binding proteins. A number of immobilized triazinyl dyes were tried and good success was obtained with only one or two. It is preferred to use either the so-called "Matrex Gel Green A®" or the "Cibacron® Blue 3G-A". Most preferred is Matrex Gel Green A having the following formula:

These dyes and their appropriate immobilized counterparts are described in a booklet by Amicon entitled: "Dye-Ligand Chromatography: Applications, Method, and Theory of Matrex TM Gel Media", by Fulton, S. (ed. by M. Marois), Publication 512 A, 1st Edition, Amicon, 1980; herein incorporated by reference.

After equilibrating the chromatographic dye-containing column with the WGL-II material, the column is washed approximately 5-20 times per volume to remove unbound proteins. The bound fraction containing the MIS biological activity, is eluted by increasing the inorganic salt concentration of the starting buffer, to a level sufficient to desorb said MIS from said dye. The starting inorganic salt concentration is normally 0.01–0.2M, and is at a level which allows binding of MIS fraction to the dye. The desorption inorganic salt concentration is normally about 1.0M. The column can be regenerated following its use with 5M guanidine hydrochloride, and stored in PBS.

All chromatographic fractions are concentrated by ultrafiltration and dialyzed against PBS at 4° C. for at least 24 hrs. before bioassay via the organ culture described below.

Table I, supra summarizes the degree of purification and biological activity of MIS-containing fractions obtained throughout specific embodiments of the present purification procedures. More than 7,000-fold purification is achieved following lectin chromatography and concanavalin A. The value shown for testis tissue in Table 1 is based on a dry weight of 350 mg/testis, obtained by lyophilizing testes from 1-2 week old calves and averaging 3 separate determinations.

Biological activities of all column fractions are determined using the organ culture assay adapted by Donahoe et al (J. Surg. Res. 23:141–148 (1977) from the procedure of Picon (Arch. Anat. Microsc. Morphol. Exp. 58:1–19 (1969), both of which publications are herein incorporated by reference in their entirety). Bioctivity of 1-2 mm fragments of newborn calf testes tissue yield better than a 4+ grade regression by direct co-culture. Since the assayed fragment is only a small fragment of the whole, one gonad would be expected by extrapolation to yield complete or 5+ regression, as indicated in Table 1. Also listed in Table 1 are the MIS bioactivities of positive fractions resulting from the purification procedure. Incubation media and fractions of DEAE-I and CM-I consistently yield very high biological activity in the 3-4+ range with no diminution as the purification proceeds.

Results obtained with bound glycoprotein fractions from lectin affinity chromatography WGL-II and Con A-II show that the MIS bioctivity is somewhat reduced in relation to the preceeding steps. All column fractions not otherwise summarized in Table 1 consistently give similar negative responses.

Figure 1:
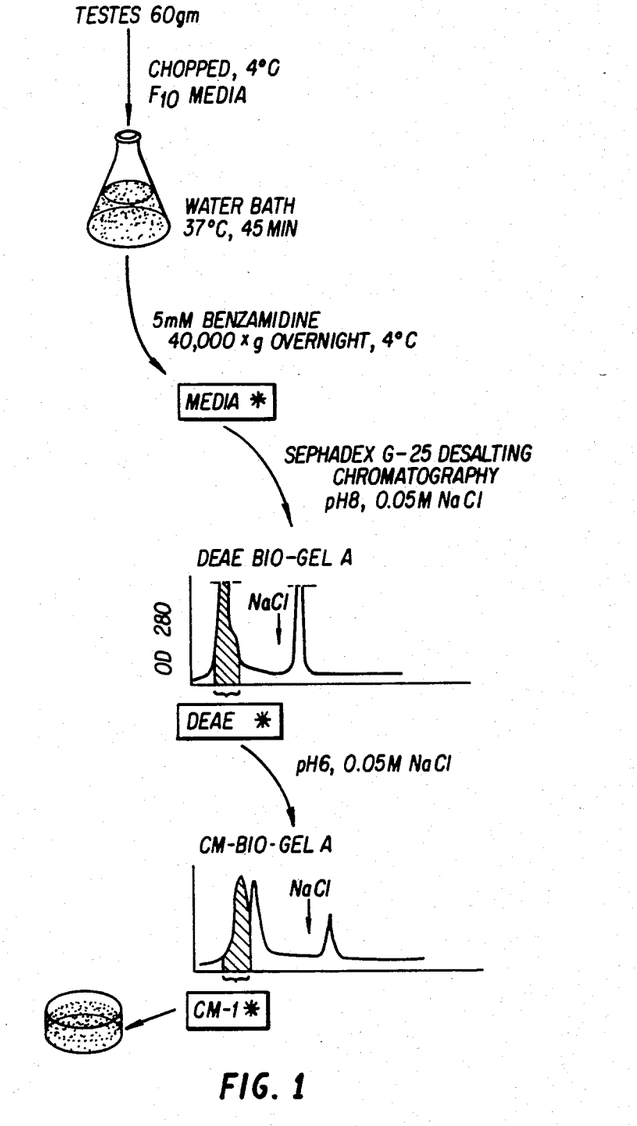
FIG. 1 shows the part of the sequential steps in the purification of Mullerian Inhibiting Substance including (sequentially): Incubation, anion exchange and cation exchange chromatography. The 50-fold purified CM-1 fraction was further purified either by using wheat germ lectin and Concanavalin A affinity chromatography in a sequential two-step process or alternatively, by wheat germ lectin and dye affinity chromatography in a sequential two-step process. (Not shown).
Figure 2:
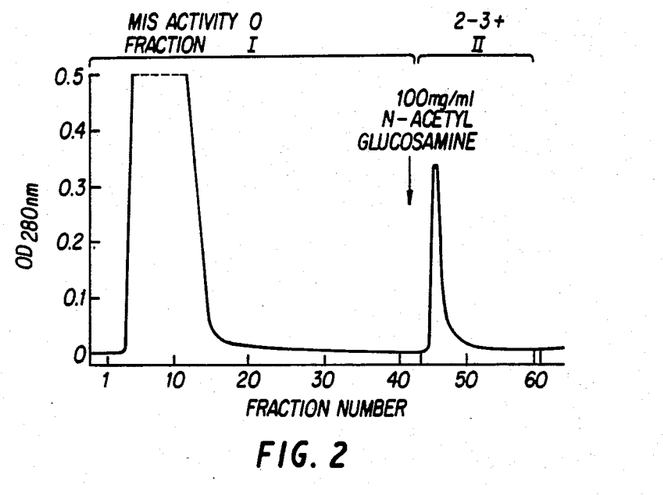
FIG. 2 shows wheat germ lectin-sepharose 6MB affinity chromatography of the CM-1 fraction of FIG. 1. The lectin gel was packed in a column (0.9×13 cm) and equilibrated with phosphate buffered saline (PBS) (0.15M sodium chloride, 10 mM sodium phosphate (pH 7.0)) at 10 ml/hr. 3-fold concentrated fraction CM-1 was loaded and 5 ml fractions were collected. Bound glycoprotein was eluted with N-acetyl glucosamine (100 mg/ml in PBS as indicated). Protein elution was monitored at 280 nm and the active fraction is shaded.
Figure 3:
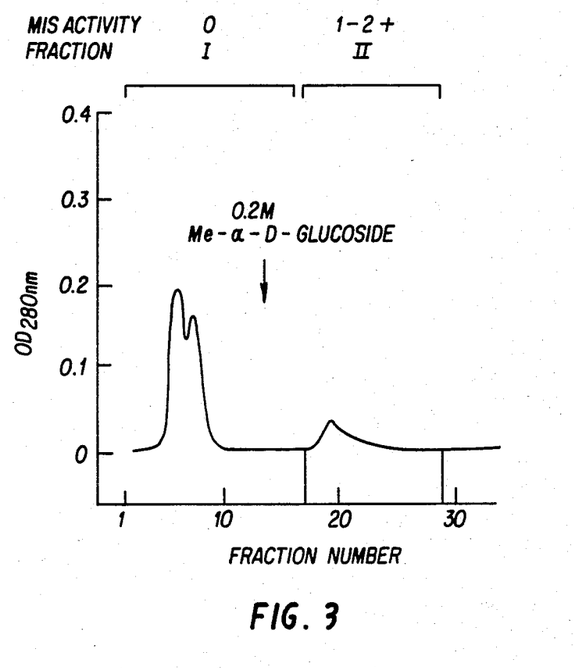
FIG. 3 shows the concanavalin A-Sepharose 4B affinity chromatography. A column (2.5×10 cm) was prepared with the lectin matrix and equilibrated with PBS at 50 ml/hr. Concentrated wheat germ lectin fraction II (see FIG. 2, "WGL-II") was loaded directly, and 8 ml fractions were collected. Elution was completed with 1-O-methyl-α-D-glucopyranoside (0.2M in PBS) as indicated. Effluent absorbance was followed at 280 nm, and the active fraction is shaded.
Figure 4:
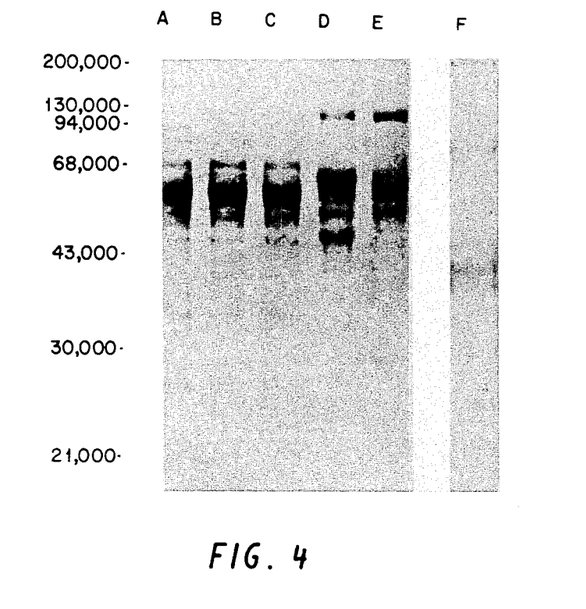
Figure 5:
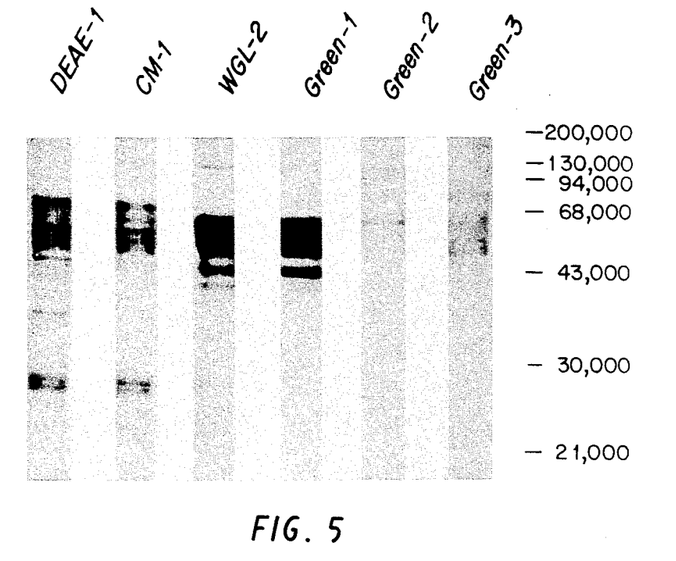
FIG. 5 shows the gel patterns for same fractions as in FIG. 4 (under same conditions), with the addition of the MIS composition purified by dye affinity chromatography.

The five biologically active fractions were analyzed by SDS-polyacrylamide/gel electrophoresis (see FIGS. 4 and 5). The early stage fractions show a large number of protein components. Fraction Con A-II which is purified more than 7,000-fold contains a greatly reduced number of bands localized at three regions of the gel. Single bands are found at approximately 130K and 30K Daltons, and a group of bands is found between 70K and 50K Daltons. When Con A-II is electrophoresed under identical conditions, but without prior reduction by 2-mercaptoethanol, a very similar band pattern emerges although the mobilities of some components are slightly higher.

Amino acid analysis of fraction Con A-II verifies the protein character of the sample.

As expected from their lectin affinities, all components of fractions WGL-II and Con A-II stain with periodic acid-Schiff reagent on comparable gels, indicating the glycoprotein nature. The carbohydrate analysis of fraction Con A-II indicates a total sugar content of 8.3% (W/W). As expected from the sequential affinity of this MIS-containing fraction for wheat germ lectin and concanavalin A, both 2.8% N-acetyl glucosamine and 0.7% mannose are detected. In addition, 1.3% galactose, 0.9% galactosamine and 2.6% N-acetyl neuraminic acid are obtained in the same analysis.

The Con A-II material is substantially free of albumen and has the polyacrylamide gel electrophoresis profile and pattern substantially shown in FIG. 4E. In addition to this, the material obtained by chromatography on the dye chromatographic step is also substantially free of proteinaceous materials having molecular weights in the range of 35,000±10,000 and 70,000±10,000 and has the polyacrylamide electrophoresis profile and pattern substantially as shown in FIG. 5. These two materials constitute preferred embodiments of the present invention.

The highly purified active MIS-rich fractions of the present invention exhibit profound effects on the inhibition of growth or the selective destruction of transformed ovarian cells and tumors (see corresponding FIGURES). The active MIS-rich fractions of the invention are administered to animal cells including human cells in tissue culture in a standard microcytotoxicity system to cancer cells derived from a human papillary cystadeno carcinoma. Generally, the dosage of administration is at least about 100 picograms purified MIS-rich fraction per gram of excised whole tissue. In addition, clinical studies in patients with ovarian carcinoma also demonstrate that the purified fractions of the present invention control cancer cell colony growth.

Administration to a patient suffering ovarian carcinoma can be intraperitoneal (if disease is at a stage where ascites fluid is present); intratumoral or by injection (if a mass is present), or by perfusion into a tumor-adjacent artery. Dosages will depend on the age of the patient, side effects, condition of the patient, advanced stage of the carcinoma, and other such factors readily determined by those skilled in the art. Quite obviously, the higher the purification stage of the MIS material, the less dosage is needed to achieve an equivalent result. Ideally, dosages would range from 1 to 1000 ng/kg, most preferably 10 to 500 ng/kg.

Having now generally described this invention the same will be better understood by reference to certain specific examples which are included herein for purposes of illustration only and are not intended to be limiting of the invention unless otherwise specified.

METHODS AND MATERIALS

Organ Culture Assay System

The assay system used is described in Donahoe et al, J. Surg. Res. 23:141–148 (1977), which is the Mullerian regression organ culture assay. The urogenital ridge is dissected from a 14-day female rat embryo and transferred to an organ culture dish. Specimens are placed on stainless steel grids coated with a thin layer of 2% agar and incubated for 72 hours at 37° C. and 5% CO₂ and 95% air over 2 ml of culture medium (CMRL 1066 containing 10% fetal calf serum, 1% penicilin (10,000 units/ml)), or a 1:1 mixture of culture medium and the supernatant or gradient fraction to be tested. The incubated tissue is then coated with a mixture of 2% agar and albumin at 44° C., fixed and buffered in formaldehyde, dehydrated in ethanol, cleaned in xylene, and embedded in paraffin. 8-micrometer serial sections are stained with hematoxylin and eosin for viewing by light microscopy. Sections from the cephalic end of the Mullerian duct are assigned a coded number and graded for regression (Donahoe et al, Biol. Reprod. 15:329–334 (1976)), on a scale of 0 to 5. 5 slides with 6 to 8 sections per slide are read for each assay. The grade of activity is listed as the nearest whole number to the mean. A test group for the fractionation procedure represents at least 10 assays. If the mean falls midway between two numbers, then both numbers are listed.

Grade 0 refers to no regression. The Mullerian duct, which is lined with columnar epithelial cells whose nuclei have a basilar orientation, has a widely patent lumen.

Grade 1 is minimal regression. The duct is slightly smaller, and either the surrounding mesenchyme is condensed around the duct as seen in plastic sections, or there is a clear area around the duct as seen in paraffin sections.

Grade 2 refers to mild regression. The duct is smaller, and the mesenchymal condensation or the clear area around the duct is more pronounced. The nucleii of the shorter epithelial cells lose their basilar orientation.

Grade 3 is moderate regression. The duct is very small and disorganized. The tip of the urogenital ridge develops poorly distal to the Wolffian duct.

Grade 4 is severe regression. The duct is replaced by a whorl of cells.

Grade 5 refers to complete regression. No remnant of the duct can be detected.

Positive tissue controls, using fetal testis, and negative tissue controls, where the Mullerian ducts were incubated alone or with muscle, were included in each experiment. Mullerian ducts exposed to extracts from non-testicular tissue, to inactive testicular fractions, or to saline served as biochemical controls. Aliquots of all fractions were dialyzed against distilled water and freeze-dried, and protein content was measured.

EXAMPLE 1

Preparation of MIS fraction Con A-II.

Newborn calf testes (250 mg/testis, dry weight) were obtained at an abattoir from 1–2 week old calves. 40 testes were removed from the animals directly after slaughter and immediately dissected free of adjacent tissues. This tissue (14,000 mg/dry weight) was rapidly diced with a Mac Ilwain automatic tissue chopper, and suspended in 250 ml/ice cold Ham's nutrient media F-10 (GIBCO) without added serum. The tissue-media suspension was transported on ice and subsequently incubated in a 37° C. control water bath with gentle shaking for 45 minutes. The protease inhibitor benzamidine was added to a final concentration of 5 mM and the suspension was centrifuged at 40,000 Xg for 18 hours at 4° C. The tissue residue was discarded and the supernatant was concentrated to 40 ml. Thus, the amount of MIS as well as any other testicular product released by one testis was concentrated to 1 ml.

In preparation for anion exchange chromatography, the concentrated media was passed rapidly through a Sephadex G-25 column (2.5×45 cm) equilibrated and eluted with 0.05M sodium chloride, 10 mM sodium phosphate (pH 8.0) at a flow rate of 300 ml/hr. to adjust conditions of ionic strength and pH. This and all subsequent fractionation steps were performed at 4° C. The protein fraction was monitored by absorbance at 280 mM, pooled appropriately and concentrated to the loading volume by ultrafiltration through an ultrafiltration membrane.

The reequilibrated media was loaded on a DEAE Bio-Gel A ® column (2.5×40 cm) preequilibrated and initially eluted with the same pH 8.0 buffer, operated at a flow rate of 100 ml/hr and 17 ml fractions were collected. After the first peak returned to the 280 nm absorbance base line the buffer was changed in a step to 0.5 molar sodium chloride, 10 mM sodium phosphate (pH 8.0), to release the bound material. Column fractions were pooled and concentrated by PM 30 ® untrafiltration to the volume of loaded sample.

The pH of the biologically active pool from DEAE chromatography (DEAE-I) was gently adjusted to 6.0 with a slow addition of 1.0M hydrochloric acid and with constant stirring in preparation of cationic exchange chromatography. A fair amount of precipitation occurred during this procedure, necessitating centrifugation at 40,000 xg for 10 minutes. The supernatant was immediately loaded on a CM Bio-Gel A (Bio-Rad) column (2.5×20 cm) preequilibrated with 0.05M sodium chloride, 10 mM sodium phoshate (pH 6.0). The column was run at 70 ml/hr and 12 ml fractions were collected. The bound fraction was eluted with 0.5M sodium chloride, 10 mM sodium phosphate (pH 6.0), after the 280 nm elution profile approached background. Column fractions were pooled and concentrated by PM 30 ultrafiltration.

The biologically active fraction from CM chromatography (CM-I) was concentrated 3-fold above the 1 testes per ml concentration, and directly loaded on a wheat germ lectin-Sepharose 6 MB column (0.9×13 cm) packed and equilibrated with 10 mM sodium phosphate (pH 7.0), 0.15M sodium chloride (PBS). The column was washed with PBS at 10 ml per hour and 5 ml fractions were collected. After the eluent 280 nm absorbance reached background, the bound glycoprotein fraction was eluted with N-acetyl glucosamine (100 mg/ml in PBS). The unbound and sugar-eluted fractions were pooled and concentrated to the loading volume.

Without further equilibration, the MIS-containing bound fraction from WGL chromatography (WGL-II) was loaded on a second lectin affinity column 2.5×10 cm) containing concanavalin A-sepharose 4B previously equilibrated in PBS. Elution was continued with PBS until the 280 nm absorbance profile reached background, whereupon the final glycoprotein fraction was released with 0.2M 1-O-methyl-α-D-glycopyranoside in PBS. Fractions were pooled and concentrated to the loading volume by PM 30 ultrafiltration.

EXAMPLE 2

Preparation Of MIS Material By Dye Affinity Chromatography

The bound MIS fraction from the wheat germ lectin column (WGL-II) was concentrated and dialyzed against 10 mM sodium phosphate (pH 8.0), 0.15M sodium chloride and 5 mM 2-mercaptoethanol. This material was loaded on a 2 ml column of Matrex Gel Green A (Amicon Corp.) equilibrated with the same buffer. The column was washed with approximately 10 volumes of the starting buffer to remove the unbound proteins. The bound fraction containing the Mullerian Inhibiting Substance biological activity was subsequently eluted with 10 volumes of 10 mM sodium phosphate (pH 8.0), 1.0M sodium chloride, 5 mM 2-mercaptoethanol.

Biological Studies

EXAMPLE 3

This experiment demonstrates that MIS fraction CM-I is successful in a clonogenic soft agar assay in inhibiting growth of a human ovarian carcinoma cell line (HOC-21) in a dose dependent manner when compared to PBS media controls, heat-inactivated MIS or biochemical fractions which lack biological activity ($p<0.05$).

All fractions were assayed in the semiquantitative organ culture assay supra.

The incubation procedure consisted of testing each dose in triplicate in a separate tube with gentle shaking at 37° C. for one hour, the tube containing $7.5 \times 10^5$ HOC-21 cells in a volume of 2.5 ml enriched CMRL 1066 media, which included 0.3 ml of either (1) MIS preparation (2) inactive fractions from testis or heart, (3) heat-inactivated fractions, (4) PBS, or (5) doxorubicin 1.0 micrograms per ml in PBS. Then 45 microliters of 50 mM asparagine, 22.5 microliters of DEAE Dextran (50 mg/ml), and 11 microliters of 50 mM mercaptoethanol were added prior to plating. $7.5 \times 10^5$ cells were then passed through a #25 gauge needle. 0.53 ml of 2% Gibco ® agar was added to the 2.5 ml cell suspension to give a final concentration of 0.35% agar. After mixing, 1 ml of the solution was pipetted into each coated 35 mm grided of Petri dish (LUX #5217) and allowed to harden at room temperature for ½ hour. Plates were incubated at 37° C., in 5% carbon dioxide for 14–21 days, and colonies were counted.

Colonies, consisting of approximately 25–30 cells appeared 10 to 14 days after plating and were manually counted on an inverted phase microscope. Squares (2×2 mm) were counted in a standardized cruciate pattern by 2 independent observers. Colony inhibition by the biologically active MIS fractions (such as CM-1) at various dilutions was compared either with (1) biologically inactive fraction from the same chromatography columns, (2) heat-inactivated CM-1, (3) biologically inactive fractions from bovine heart, (4) PBS, or (5) doxorubicin. Results of these experiments were compared by the student T test. A value of $P<0.05$ was considered significant.

Figure 12:
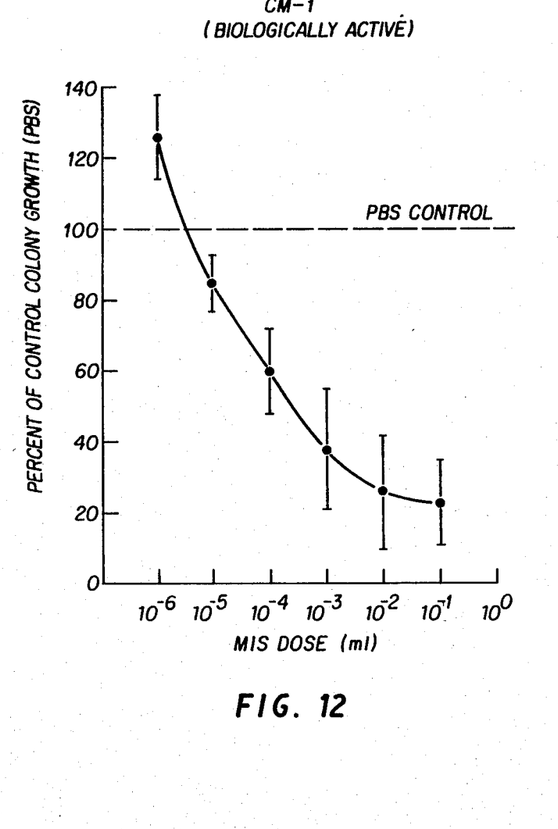
FIG. 12 shows colony inhibition by the biologically active CM-1 fraction expressed as a percentage of PBS control colony growth, and the results from multiple doses of each of 5 experiments (3 plates each) combined to form the dose-response growth. The vertical lines indicate the standard deviation at each dose. Colony growth at doses at $10^{-1}$ to $10^{-4}$ were significantly different from controls. 1 ml of CM-1 fraction MIS corresponds to the product of one testes: $3\times10^{-3}$ ml, equivalent to 2 micrograms semipurified protein, produces 50% inhibition of colony growth with PBS controls.

Fractions with high MIS biological activity as demonstrated in organ culture assay, inhibited colony growth in the soft agar colony inhibition assay in a dose-dependent manner. A significant difference was seen when CM-1 from $10^{-4}$ to $10^{-1}$ ml were compared to control PBS plates. Doses of $10^{-5}$ and $10^{-6}$ did not show significant differences. Mean colony growth of control plates was established at 100% and inhibition was calculated as a percent of controlled colony counts. A dose-response relationship was evident when the data were plotted on a semilog scale (see FIG. 12). 50% inhibition occurred with $3 \times 10^{-3}$ ml MIS preparation, which corresponded to 2 micrograms total protein or 1/300 of the purified product of a single testes. Heat inactivated CM-1 did not inhibit the colony growth significantly when compared to PBS controls. Adriamycin exhibited significant colony inhibition when compared to PBS controls and served as positive control. CM-2, the biologically inactive fraction which weakly adheres to the CM bio-gel column and was subsequently eluted with 0.5M sodium chloride, demonstrated variable but significantly less inhibition of colony growth of this variant cancer cell line than CM-1. It was elected to use heat-inactivated CM-1 rather than untreated CM-2 as a negative control since the CM bio-gel column elution may not effect complete separation of the active moiety, i.e., CM-2 may contain small amounts of active MIS. Newborn calf heart tissue was prepared in a manner identical to newborn calf testis. Human ovarian cancer cells incubated with the CM-1 fraction from heart (150 microliters with a protein concentration of 4.5 mg/ml), produced the same number of colonies (202±43), as did those cells incubated with phosphate buffered saline (202±42).

The ability of MIS to inhibit HOC-21 in soft agar in a dose-dependent manner, and to lose the ability with heat inactivation supports the concept of cytotoxicity in a microcytotoxicity assay. Fractions biologically inactive in organ culture assay are unable to inhibit HOC-21 colony growth, again demonstrating the specificity observed in the microcytotoxicity toxicity assay. The efficacy of MIS as a chemotherapeutic agent is further confirmed by these colony inhibition studies. The inhibition caused by MIS compares very favorably with that caused by adriamycin. MIS, a large molecular weight glycoprotein, is inactivated after 4 to 6 hours at 37° C., therefore, its effect on the tumor cells is fairly short. Adriamycin in contrast, is a small stable molecule. The cells in the colony inhibition assay, therefore remain continually exposed to adriamycin which provides a positive control with maximum inhibitional growth. The same dose of adriamycin might be expected to cause repeated cell damage. Since MIS rapidly loses biological activity at 37° C., sequential small doses are preferred in providing an augmented effect against sensitive cells.

EXAMPLE 4

This example demonstrates that MIS is able to inhibit growth of a human ovarian cancer in nude mice.

Athymic, hairless male and female mice (NU/NU), 4 to 6 weeks of age, from the Charles River Laboratories (BALB/c or CD1) or Harlan Industries (Swiss) were kept in sterile, convered cages in a draft free filtered and ventilated nude mouse facility at 75° F. and 45–50% humidity. The cages were supplied with sterile bedding and food, and water with multivitamins. The mice were observed for a week prior to experiments, and were handled with mask and glove technique at all times.

The human ovarian cancer cell line (HOC-21), obtained from Japan (Keio University, Tokyo, Japan), doubles every 28 hours in tissue culture. Its previous diploid number of 46 xx noted in a karyotype done in 1974, changed to a modal # of approximately 70 in 1981 after continuous serial subculture. The histological appearance of the tumor, however, has remained similar to that of the original tumor removed in 1971, if $10^4$ or more cells are heterotransplanted into the hamster cheek pouch or $10^5$ or more cells are transplanted into homozygous nude mice. Since 1978, this cell line has been subcultured twice weekly on stationary monolayers at 37° C. in Eagle's Minimal Essential Medial (MEM) containing 15% fetal calf serum, 1% penicillin (10,000 units/ml) and streptomycin (10,000 micrograms/ml).

A human carcinoma cell line (SW-48) was established from poorly differentiated colonic adenocarcinoma as described in Leibovitz, A. et al, Cancer Research, 36:4562-4569 (1976)). The cells of this tumor have a modal chromosome number of 47 and produce small amounts of carcinoembryonic antigen. Subcutaneous heterotransplantation of 6 to $10 \times 10^6$ cells in the dorsum of the nude mouse has produced tumors of similar histologic appearance.

The tumor cells were harvested when they were synchronized in the log phase of growth after multiple three-day cultures. Cells were washed twice in Hank's basic salt solution without magnesium or calcium, for 3 minutes, and trypsinized for 5 minutes at 37° C. with trypsin-EDTA (1:250). Cell clumps were disaggregated to create a single cell suspension by passage through a #25 gauge needle. The cells were counted in a hemocytometer chamber, and viability (>95%) was assessed by trypan blue exclusion.

The appropriate cell number (1 to $5 \times 10^6$) for a given group of mice was aliquoted into sterile 15 ml tubes and the contents were centrifuged at 1,500 rpm for 10 minutes. The supernatant was decanted, and the cells were washed twice with plain MEM and resuspended in enriched CMRL-1066 containing either (1) MIS preparation, (2) heat inactivated MIS, (3) a heart preparation, (4) phosphate buffered saline, (5) Doxorubicin, or cis-diaminedichloroplatinum 0.04 micrograms/ml. Cells, varying from $1 \times 10^6$ to $5 \times 10^6$/0.5 ml were incubated by gentle manual agitation with each of these substances for 1 hour at 37° C. prior to injection. The injection of 0.5 ml was done with a #25 gauge needle in the subcutaneous tissue of the mid-dorsal right flank. Selected animals were reinjected at 24 and 48 hours at the site of the original inoculation.

The animals were inspected for tumor development daily and the length and width of each tumor was measured. The earliest day of tumor appearance was noted. The animals were sacrificed at selected intervals throughout and at the conclusion of the study, and the presence or absence of tumor was confirmed histologically. The proportion of animals free of tumor in each group was plotted against time from inoculation using Kaplan-Meier life table calculations, and the significance of the delay in tumor appearance was determined by the log rank test of Mantell on a programmable calculator. Tumor-free MIS-treated animals were compared with tumor free control animals by the Fischer Exact Test, $P<0.05$ was considered statistically significant.

RESULTS

The tumors grew equally well in Swiss, Balb/C and CD1 nude mice. The Balb/c strain, however, survived repeated handling without the development of a wasting disease. The experiments were done in either Balb/C or Swiss mice. Tumor grew at similar rates in Balb/C males, Balb/C females and gonadectomized Balb/C males, except in cages where the males were cannibalistic. The unbitten dominant male in these cages exhibited tumor growth at a normal rate. Because of the observation of this "pecking" phenomenon, female mice were used for the definitive experiments.

Tumors grew readily in control animals, invading locally but not metastasizing. Nodules of 3 to 4 mm in diameter could be palpated at 48 hours. Subsequently either central necrosis and tumor regression occurred, or the tumors grew logarithmically. The pattern of growth depended on the cell number of the inoculum. Those animals that received 1 to $1.5 \times 10^6$ cells had regression of their tumors, but the tumors growing in animals receiving $>2 \times 10^6$ cells persisted and continued onward to log growth. Histologically confirmed nodules, 3 to 4 mm in diameter, should have a total volume of 14–32 mm$^3$. If an individual cell 20 microns in diameter has a volume of approximately $4\times 10^6$ mm$^3$, then 3.5 to $8.4\times 10^6$ HOC-21 cells were calculated to be present in the nodule. Therefore, if $2\times 10^6$ cells were injected, this number of cells must have resulted from approximately two cell divisions; such a conclusion is consistent with the kinetics of the HOC-21 tumor observed in tissue culture.

Figure 6:
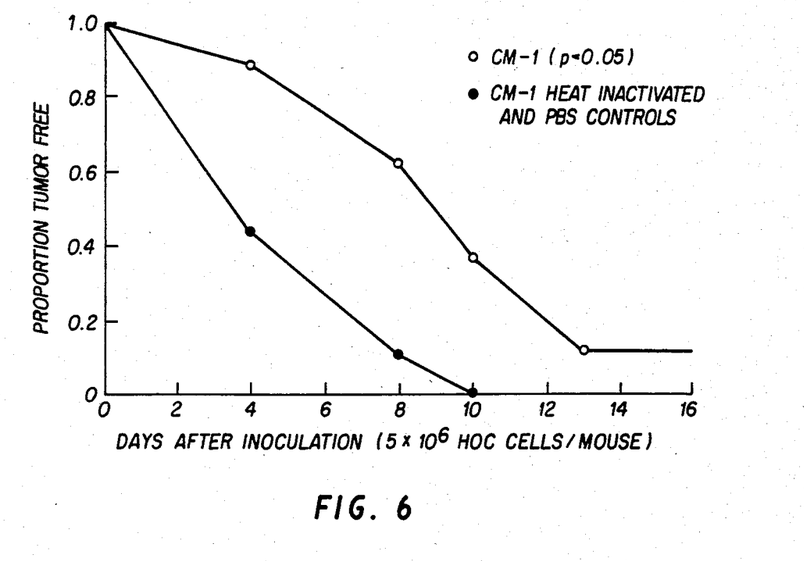
FIG. 6 shows that incubation of $5\times10^6$ cells from a HOC-21 cell line with biologically active CM-1 MIS fraction (see FIG. 1) (-o-) prolonged the tumor free interval in BALB/C nude mice compared to incubation with heat inactivated MIS and PBS (-●-).

In a preliminary experiment (FIG. 6) $5\times 10^6$ HOC 21 cells were injected into Balb/c nude mice after pretreatment of the cells with 0.02 to 0.5 ml of MIS preparation per animal. A statistically significant delay in appearance of tumor was observed when pretreatment with MIS (n=8) was compared with pretreatment with heat inactivated MIS or PBS (n=9). A cell inocculum of $2\times 10^6$ or $1.5\times 10^6$ produced tumors in all the control mice whereas an inoculum of $1\times 10^6$ produced tumors in only 60%.

Figure 7:
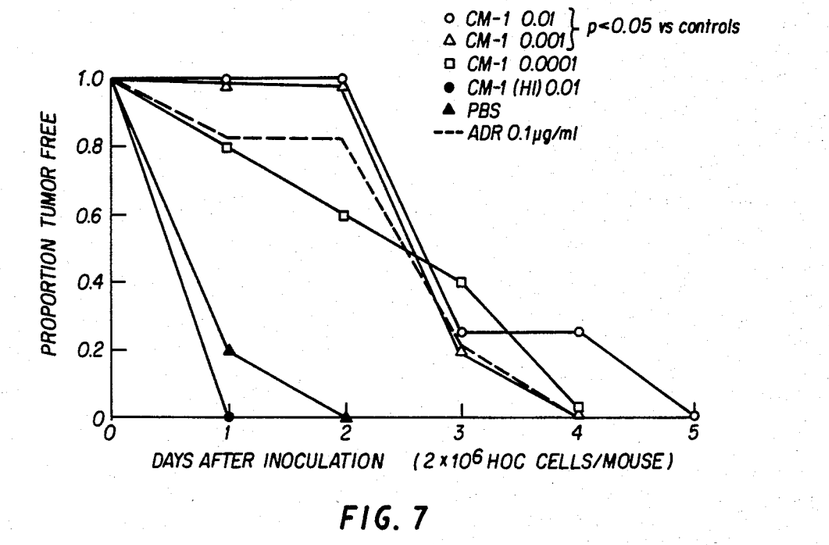
FiG. 7 shows that increase in concentrations of MIS fractions CM-1 (see FIG. 1) prolonged the tumor free interval ($P<0.05$) in Swiss nude mice. A similar prolongation is seen after pretreatment of the cells with adriamycin. Heat inactivated MIS did not prolong the tumor free interval in comparison to PBS. Each group tested consisted of 5 mice except at the highest dose where the number of mice was 4.
Figure 8:
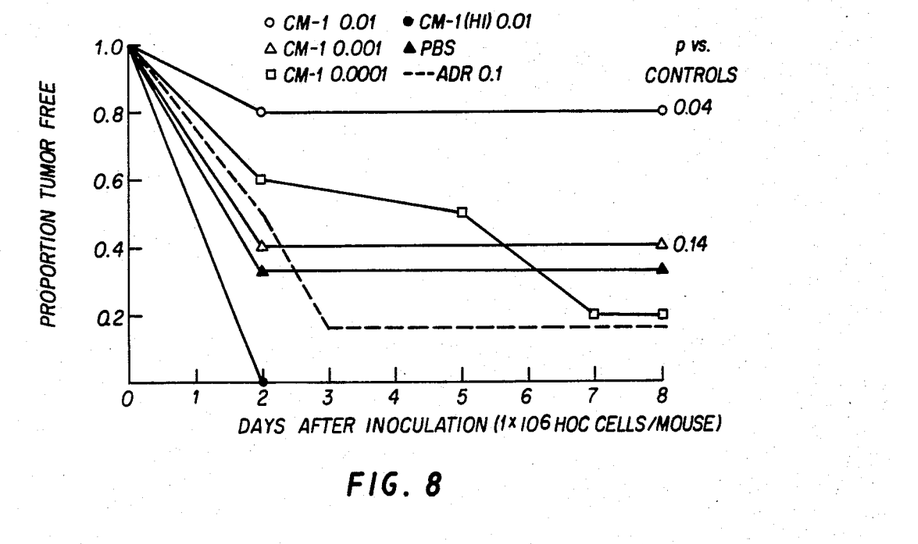
FIG. 8 shows that pretreatment of $1\times10^6$ HOC-21 cells with increasing concentrations of MIS fraction CM-1 prolongs the tumor free interval in a dose dependent manner in Swiss nude mice. The highest concentrations of CM-1 at this cell number resulted in 80% tumor free survival ($P=0.04$). $N=5$ in each group except for the PBS treated group where $N=6$.
Figure 9:
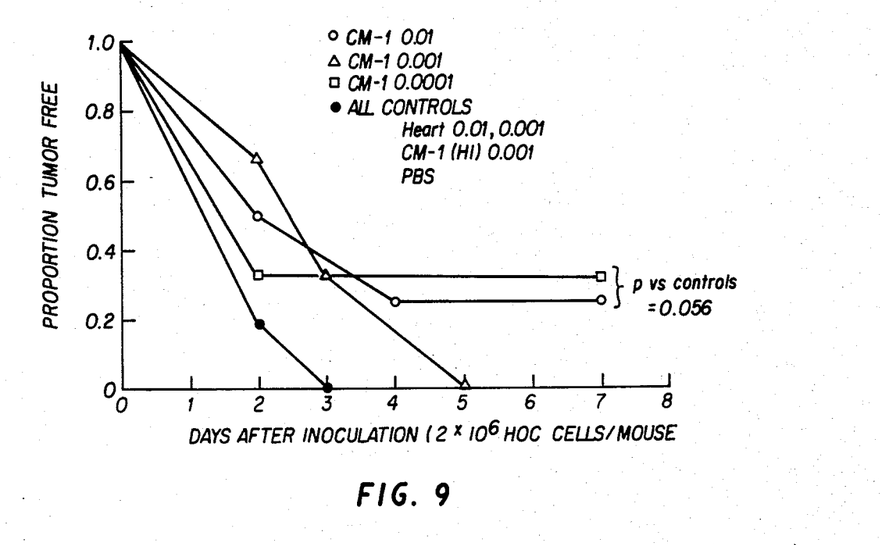
FIG. 9 shows that the proportion of tumor free mice after treatment with 0.01 ml as a single dose, or three doses of 0.001 ml CM-1 (MIS) was increased at a rate approaching statistical significance. Curves for the heart preparation, heat inactivated CM-1 and PBS treated animals were identical. Each group consisted of 3 or 4 animals.

$2\times 10^6$ cells were present in the inoculum used in the experiments of FIG. 7 (n=29), which explored the effects of varying doses of MIS on tumor growth with 5 mice in each group. An MIS dose response relation was observed both when the time of appearance of the tumor and the tumor free survival of the animals were evaluated (FIGS. 7 and 8). Pretreatment with Adriamycin also delayed the appearance of the ovarian tumor (FIGS. 7 and 8). A biologically inactive preparation from bovine heart, purified in the same manner as the CM-1 preparation of MIS from bovine testes, did not prolong the tumor free survival (FIG. 9), but produced a curve of time to tumor appearance identical to that of the heat inactivated CM-1 (FIGS. 7, 8 and 9) or PBS. Injection of 0.001 ml MIS in 0.5 cc at the original inoculation site 24 to 48 hours later, resulted in a proportion of tumor free animals equivalent to that achieved by a single pretreatment of tumor cells with 0.01 ml of MIS (FIG. 9). The tumor nodules were sampled histologically for confirmation at the end of the experiment in all the animals, and at two days, three days, and five days after injection in selected control animals. The histologic appearance was similar to that seen in the original tumor.

Figure 10:
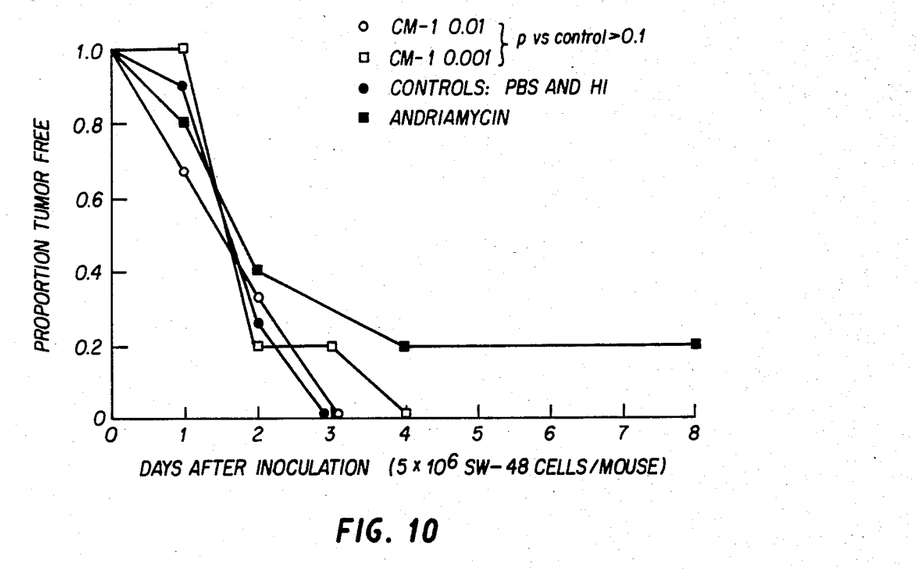
FIG. 10 shows that pretreatment of colon carcinoma cells ($5\times10^6$) with MIS did not delay tumor appearance when compared with PBS or heat inactivated MIS. $N=6$ in each group.
Figure 11:
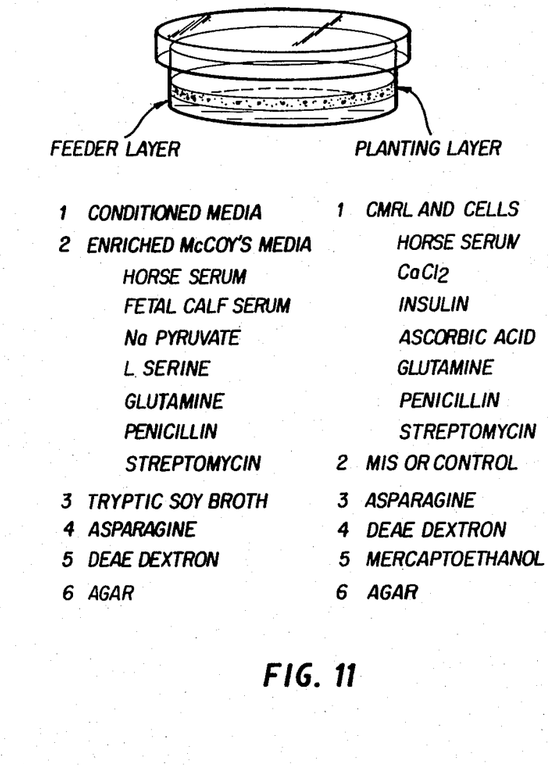
FIG. 11 shows a schematic description of the colony inhibition assay which employs a 2-layer agar plate with a feeder layer containing a conditioned media and a plating layer containing cells and MIS or control. (See Examples for further descriptions).

An inoculum of $5\times 10^6$ human colon carcinoma cells (SW-48) was required to produce a palpable tumor in all the control animals within 5 days. $1\times 10^6$ cells produced a tumor in only 40%, and $2\times 10^6$ cells in only 60% of the animals injected. Pretreatment of the SW-48 cells with MIS resulted in no delay in the appearance of the tumor in comparison to that observed with the use of PBS or heat inactivated MIS (FIG. 10).

EXAMPLE 5

Figure 13:
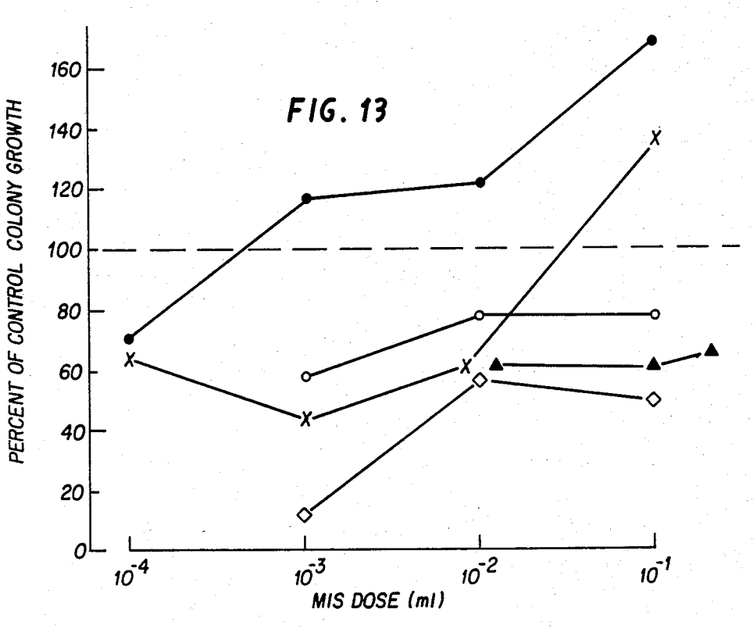
FIG. 13 shows the percent of control colony growth as a function of MIS dose fraction CM-I of FIG. 1. Ascites fluid was tapped from 5 patients with ovarian carcinoma. The Figure shows that 4 out of 5 patients' cells show inhibition of colony growth after preincubation with MIS.

This experiment demonstrates that human ovarian carcinoma cells will be inhibited in their growth when cultured in the presence of MIS. Five female patients with Stage 4 ovarian carcinoma were used, their ascites fluid was tapped and tumor cells harvested therefrom and grown on colony with MIS fraction CM-1 or with PBS as control. FIG. 13 shows the results. Four out of five tumor cells responded positively (i.e., growth was suppressed) in the presence of MIS.

Having now fully described this invention, it will be appreciated by those skilled in the art that the same can be performed within a wide range of equivalent parameters of composition, conditions and modes of administration without departing from the spirit or scope of the invention or of any embodiment thereof. What is new and intended to be covered by Letters Patent of the United States is:

We claim:

1. A composition comprising Mullerian Inhibiting Substance (MIS) derived from testicular tissue having an activity of at least 1 as measured by the Mullerian organ regression test being substantially free of albumen and being about 7,000–8,000-fold enriched in MIS activity over natural testicular tissue per dry weight of tissue.

2. A composition comprising Mullerian Inhibiting Substance (MIS) derived from testicular tissue having an activity of at least 2–2.5 as measured by the Mullerian regression organ test; being substantially free of albumen and of proteinaceous material having a molecular weight of $35,000\pm 10,000$ Daltons and $70,000\pm 10,000$ Daltons, being about 15,000-fold enriched in MIS activity over natural testicular tissue per dry weight of said tissue.

3. A method of suppressing the growth of human ovarian cancer cells which comprises contacting said cells with a growth suppressing amount of the MIS composition of any of claims 1 or 2.

* * * * *